(12) United States Patent
Loustauneau et al.

(10) Patent No.: US 9,044,176 B2
(45) Date of Patent: Jun. 2, 2015

(54) DENTAL X-RAY UNIT PROVIDING A CEPHALOMETRIC IMAGE AND ASSOCIATED METHOD

(75) Inventors: Vincent Loustauneau, Fontenay sous Bois (FR); Sylvie Bothorel, Paris (FR); Jean-Marc Inglese, Bussy Saint Georges (FR)

(73) Assignee: Carestream Health, Inc., Rochester, NY (US)

( * ) Notice: Subject to any disclaimer, the term of this patent is extended or adjusted under 35 U.S.C. 154(b) by 250 days.

(21) Appl. No.: 13/514,069

(22) PCT Filed: Dec. 15, 2010

(86) PCT No.: PCT/FR2010/052752
§ 371 (c)(1),
(2), (4) Date: Jun. 6, 2012

(87) PCT Pub. No.: WO2011/080460
PCT Pub. Date: Jul. 7, 2011

(65) Prior Publication Data
US 2012/0243662 A1 Sep. 27, 2012

(30) Foreign Application Priority Data
Dec. 16, 2009 (FR) ...................................... 09 59083

(51) Int. Cl.
*A61B 6/14* (2006.01)
*A61B 6/06* (2006.01)
*A61B 6/00* (2006.01)

(52) U.S. Cl.
CPC ... *A61B 6/14* (2013.01); *A61B 6/06* (2013.01); *A61B 6/4085* (2013.01); *A61B 6/4441* (2013.01); *A61B 6/463* (2013.01); *A61B 6/488* (2013.01); *A61B 6/5247* (2013.01); *A61B 6/542* (2013.01)

(58) Field of Classification Search
CPC ............ A61B 6/14; A61B 6/06; G01N 23/00; G01N 23/04; G21K 1/02; G21K 1/04
USPC ................................ 378/38, 62, 63, 147–151
See application file for complete search history.

(56) References Cited

U.S. PATENT DOCUMENTS

| | | | |
|---|---|---|---|
| 4,603,427 A | 7/1986 | Alpern et al. | |
| 5,970,112 A | 10/1999 | Hsieh | |
| 6,778,636 B1 | 8/2004 | Andrews | |
| 7,344,305 B2 * | 3/2008 | Kuzmanovic ................. | 378/206 |
| 2003/0235265 A1 | 12/2003 | Clinthorne et al. | |
| 2004/0202283 A1 | 10/2004 | Okumura et al. | |

FOREIGN PATENT DOCUMENTS

| | | |
|---|---|---|
| JP | 2005-021661 | 1/2005 |
| JP | 2011-041598 | 3/2011 |
| WO | 2008/113715 A1 | 9/2008 |

OTHER PUBLICATIONS

International Search Report, Application No. PCT/FR2010/052752, dated Mar. 17, 2011, pp. 2.

* cited by examiner

*Primary Examiner* — Jurie Yun

(57) ABSTRACT

A dental x-ray unit comprising: an X-ray generator adapted to generate an X-ray beam in the direction of a patient's head, means of collimation adapted to confer given dimensions to the generated X-ray beam; a sensor placed facing the generator, receiving the radiologic projection of the collimated beam having irradiated the patient's head and supplying a cephalometric image of the patient's head, characterized in that the device includes: the means to acquire at least one photographic image of the patient's head, the means of automatic control for the means of collimation according to the at least one photographic image so that the dimensions of the collimated X-ray beam are adjusted to the dimensions of the patient's head.

16 Claims, 6 Drawing Sheets

DENTAL X-RAY UNIT PROVIDING A CEPHALOMETRIC IMAGE AND ASSOCIATED METHOD

FIELD OF THE INVENTION

This invention concerns a dental x-ray apparatus and an associated method.

BACKGROUND OF THE INVENTION

In the field of dental radiology, taking cephalometric shots of the head of a patient with a facial and/or profile view is known.

Such images are obtained from an x-ray unit which includes an x-ray generator and an x-ray sensor. The sensor is placed facing the generator and the head of the patient is placed between the generator and the sensor.

The generator emits radiation in the form of a cone beam x-ray in the direction of the head of the patient and the sensor receives the radiation having irradiated the head.

This received radiation makes it possible to obtain a full projection of the cranium (hard tissue) of the patient which constitutes a cephalometric shot.

This projection is obtained by scanning the head of the patient in a continuous movement synchronized between a collimation slot and the sensor, for example, in the form of CCD linear array arranged behind the head.

This type of scanning takes approximately 10 seconds.

SUMMARY OF THE INVENTION

In order to reduce the cone effect of the x-ray beams which results in significant geometric distortions (the side of the cranium situated closest to the sensor is larger than the opposite side of the cranium), the sensor is placed at a distance that is sufficiently far away from the generator (for example 1.60 m, if not more) and the head of the patient is placed closer to the sensor than to the generator.

From one or more cephalometric shots, (profile, face . . . ) a practitioner, for example, an orthodontist, may establish a diagnosis as to the existence of certain defects needing to be corrected in the patient. The practitioner then takes the measures and/or carries out scans in order to determine what corrections are needed and the appropriate treatment.

To be able to preview the effects during the correction time and treatment foreseen on the patient's face, one or more photographs of the face will be taken.

Thus, in practice, the practitioner will take a photographic image, for example, of a profile view of the head of the patient, and will only retain the outline.

This image is then superimposed by software upon the cephalometric shot taken of a view of the profile of the patient's head.

From the moment in which the practitioner determines the corrections and the treatment adapted for the patient, he is able to simulate their effects on the face of the patient and display them.

More specifically, the software available to the practitioner enables him to display, upon a first image corresponding to the current state of the patient, the photographic image representing the soft tissue of the cranium (nose, lips . . . ) superimposed onto the cephalometric shot representing the hard tissue (bone, teeth . . . ).

The software then makes it possible, by calculation, from the data selected by the practitioner when he determines the corrections and the appropriate treatment, to accordingly reshape the cephalometric shot in order to simulate the corrections and the treatment selected for the hard tissue that will take place over time.

The photographic image will also be reshaped in the corresponding manner by a morphing algorithm.

The software also allows one to view a second image by superimposing the reshaped photographic image and the cephalometric image and that represents the evolution of the patient's head after the corrections and treatment.

In this way, the evolution of the treatment may be precontrolled by visualizing the two images simultaneously.

However, so that the photographic and cephalometric images may be superimposed in a satisfactory manner, the applicant discovered that the images must be taken at the same angle of view.

Furthermore, the X-ray generator is equipped with a collimator the dimensions of which are calculated to adapt to a head having average dimensions.

However, the applicant has discovered that human heads widely range in size.

Thus, for a person with a head that is larger than the aforementioned average dimensions, the cephalometric images would show a truncated skull.

On the other hand, cephalometric image(s) obtained for a head whose dimensions are smaller than the average dimensions will show the entire skull as well as an area of the outline that is unnecessary.

As a result, the person will receive an overdose of unnecessary radiation.

This invention seeks to remedy at least one of the disadvantages mentioned above by proposing a dental radiology device including:

an X-ray generator adapted to generate an X-ray beam in the direction of a patient's head, means of collimation adapted to confer the generated given dimensions to the X-ray beam;

a sensor placed facing the generator, receiving the projection of the collimated beam of radiation having irradiated the patient's head and providing a cephalometric image of the head of the patient, characterized in that the device includes:

a means to acquire a photographic image of the patient's head, a means of automatic control for the means of collimation as a function of the at least one photographic image so that the dimensions of the collimated X-ray beam are adjusted to the dimensions of the patient's head.

By acquiring one or more photographic images of the patient's head, and, more specifically, of his/her profile and by collimating the x-ray beam so that it interlocks with the image or the photographic images thus acquired, it is possible to adjust the dimensions of the collimated beam to the dimensions of the patient's head, and, more specifically, to the dimensions of his/her profile.

A photographic image or photograph of the head of a patient captures the visible parts of the head and face, and in particular, the contour of the head (in a facial or profile view). In general, such an image is thus representative of the soft tissue of the patient's head (nose, lips . . . ). Such an image does not capture the hidden parts of the head and which represent in particular the hard tissue (bone, teeth . . . ). These parts are in fact captured by the radiological sensor which receives the x-ray that irradiated the patient's head. Such a sensor provides a cephalometric image of the head of the patient which is thus different from the aforementioned photographic image.

It should be noted that the means of acquiring the photographic image(s) are separate from the radiation sensor which form a means to acquire the cephalometric image(s).

According to one characteristic, the sensor is a pixel matrix surface sensor with dimensions that encompass the dimensions of the x-ray beam projection having irradiated the head of the patient. The acquisition of the radiological projection is performed instantly.

According one characteristic, the X-ray generator includes an X-ray emission chamber; the means of acquiring at least one photographic image is positioned as close as possible to the chamber.

By placing the means of image acquisition as close as possible to the x-ray chamber, one is assured thusly that the photographic and the cephalometric images will be taken at the same angle or, at any rate, at a very close angle taking into account given the distance between the x-ray emission chamber and the patient's head is relatively remote.

It is advisable to note that the distance between the means of acquisition of at least a photographic image and the emission chamber should be short compared to the distance between the chamber and the patient head.

This distance should be for example within a ratio of 1 to 15.

According to one characteristic, the means of collimation includes a collimator with an adjustable slot.

It is thus particularly easy to automatically control the means of collimation in function of the photographic image(s) acquired by carrying out the adjustment of the slot in an appropriate manner.

According to one characteristic, the adjustable slot collimator comprises the means to adjust the length of the slot perpendicularly between them.

According to one characteristic, the means for adjustment is directionally independent, which gives great flexibility to the adjustment.

According to one characteristic, the adjustable slot is delimited by four edges that slide in a manner that is independent from each other.

According to one characteristic, the equipment includes means to obtain the outline of the patient's head from which at least one photographic image is acquired.

This outline contains sufficient information to allow automatic control of the means of collimation.

According to one characteristic, the means of automatic control is adapted to automatically control the means of collimation in function of the dimensions of the outline of the patient's head so that the dimensions of the collimated x-ray beam are adjusted to the dimensions of the outline of the patient's head.

Dimensions of the collimated beam, and in particular the width of the beam at its base which is close to the emission chamber, can be controlled according to the contour of the head of the patient thus obtained.

This makes it possible to adjust the dimensions of the collimated beam to the dimensions of the outline of the patient's head.

The invention also has for its object a method, correspondingly, a method to produce a cephalometric image of the head of a patient comprising the following stages:

generation by an X-ray generator of an X-ray beam in the direction of a patient's head, collimation of the x-ray beam generated in order to confer to it the given dimensions, reception by a sensor facing the radiological projection of the collimated beam which irradiated the head of the patient, provision of a cephalometric image from the received radiological projection, characterized in that the method also comprises the following stages:

acquisition of at least one photographic image of the patient's head, automatic control of the collimation of the x-ray beam in function of said at least one photographic image in order for the dimensions of the collimated x-ray beam to be adjusted to the dimensions of the patient's head.

The process according to the invention has the same advantages as those described briefly above in reference to the dental x-ray unit and therefore, will not be repeated here.

According to one characteristic, the sensor is a pixel matrix surface sensor with dimensions that encompass the dimensions of the x-ray beam projection having irradiated the head of the patient, as the acquisition of the radiological projection being performed instantly.

According to one characteristic, the automatic control stage of the collimation of the x-ray beams as a function of said at least one photographic image includes the adjustment of the dimensions of the beam.

According to one characteristic, the x-ray generator includes an x-ray emission chamber, the acquisition of said at least one photographic image being performed from a position that is as close as possible to the chamber.

According to one characteristic, the automatic control stage of the x-ray beam as a function of said at least one photographic image includes the adjustment of the dimensions of the beam.

According to one characteristic, the adjustment of the dimensions of the beam comprises more in particular, the means to adjust the length of the collimation slot perpendicularly between them.

According to one characteristic, the method includes means to obtain the outline of the patient's head from which at least one photographic image is acquired.

According to one characteristic, the automatic control of the collimation is performed as a function of the dimensions of the outline of the patient's head so that the dimensions of the collimated x-ray beam are adjusted to the dimensions of the outline.

BRIEF DESCRIPTION OF THE DRAWINGS

The other characteristics and advantages will be better apparent through the description that follows, given only as a non-restrictive example and made in reference to the attached drawings in which.

DETAILED DESCRIPTION OF EXEMPLARY EMBODIMENTS

Figure 1:
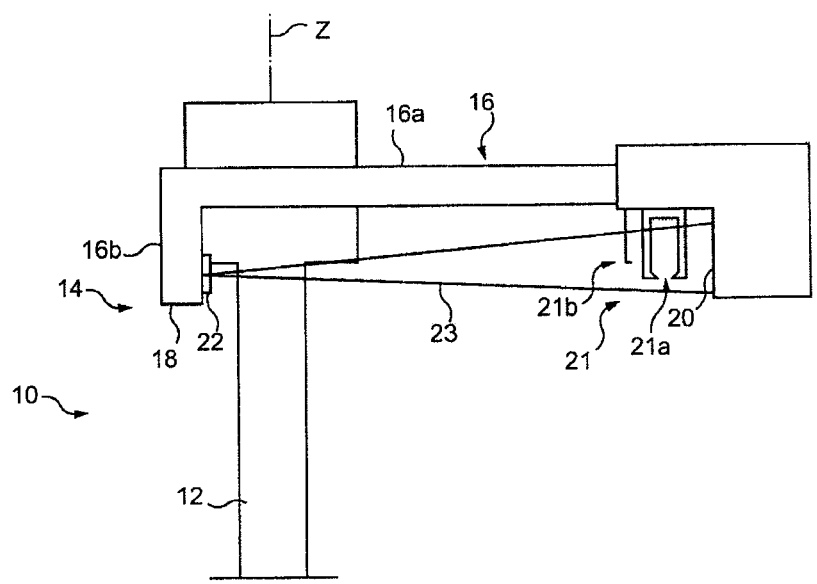
FIG. 1 is a general diagrammatic view of the device in accordance with the invention.

As shown in FIG. 1 and designated by the noted general reference (10), a dental x-ray unit according to the invention is a cephalometric type of device. This device allows cephalometric images or shots to be produced of the head of a human being. The device includes a fixed frame (12), for example a vertical bracket aligned along the axis Z, on which an x-ray unit (14) is assembled which will now be described.

This unit includes a structure (16) comprising a horizontal beam (16a) which forms a support that comprises, on one end, a vertical arm (16b) dropping from the horizontal beam, and, at the opposite remote end, an arm (16c) that is both horizontal and vertical.

A source or generator of x-rays (18) is fix mounted on the arm (16b), while an x-ray sensor (20) is mounted on the remote arm (16c) which allows the sensor to be positioned at a good distance from the generator, for example at 4 m from it.

The generator (18) and the sensor (20) are thus placed facing each other and are placed in a fixed geometric relation with respect to each other.

The structure (16) that acts as a support for the generator (18) and the sensor (20) constitutes the core of the x-ray unit (14).

The x-ray device (10) also comprises a positioning device (21) fixed upon the arm (16c) in front of the sensor (20) and which makes it possible to immobilize the head of the patient while the x-ray films are taken, during the operation of the equipment. The head is placed between the generator (18) and the sensor (20). More specifically, the device (21) comprises one part, a vertical descending positioner (21a) the two branches of which have free ends which are opposite each other, and designed to be positioned in the ears of the patient and, another part, a descending vertical beams (21b), designed to come into contact with the forehead of the patient in order to prevent back and forth movement of the head.

The x-ray generator is equipped with a support (22), placed against the face of the generator that is opposite the sensor (20) and within which an opening for the output of X-rays from the generator is arranged.

The support is positioned in from of this x-ray output opening and comprises the means of collimation that will be described in reference to FIGS. 2a and 2b.

The collimated x-ray beam has a cone form (23) that was truncated by its passage through the slot opposite the rectangular section. This beam is positioned on its base (in a section parallel to the plane of the slot), along a direction that corresponds to the direction in which the slot is laid out.

The sensor (20) fastened to the arm (16c) is positioned opposite the generator (18). It is capable, on the one hand, to receive the x-ray coming from the generator and having irradiated the object (patient's head) placed between the generator and the sensor and, on the other hand, to convert this x-ray which has been attenuated by its passage through the object into an electrical signal representative of an x-ray image of this object.

It should be noted that the sensor consists of a pixel matrix which is arranged in correspondence with the beam emitted from the collimation slot.

This sensor is, for example, a form of a phosphor scintillator including the active surface pixel matrix and its dimensions are for example, 30 cm (height)×30 cm (width). The pixel matrix have for example a size of 150 pm and thus form a matrix of 2000×2000 pixels. Alternately, the sensor is constituted of a pixel matrix with a CCD-type charge-transfer with a size of, for example, 5 cm×5 cm and which is provided with an optical focus with an optical zoom of 6. The design includes an electronic control and power supply located behind it.

Figure 2A:
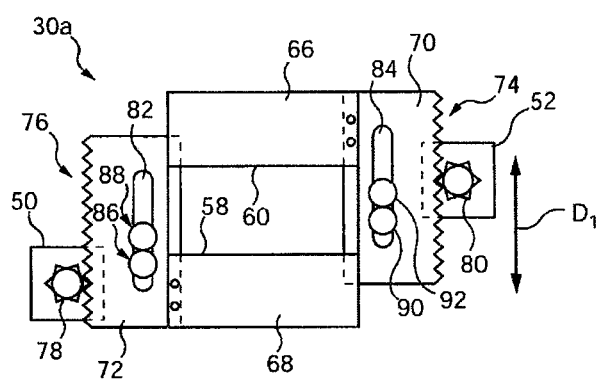
FIGS. 2a and 2b respectively illustrate the means of collimation used in the device of FIG. 1.
Figure 2B:
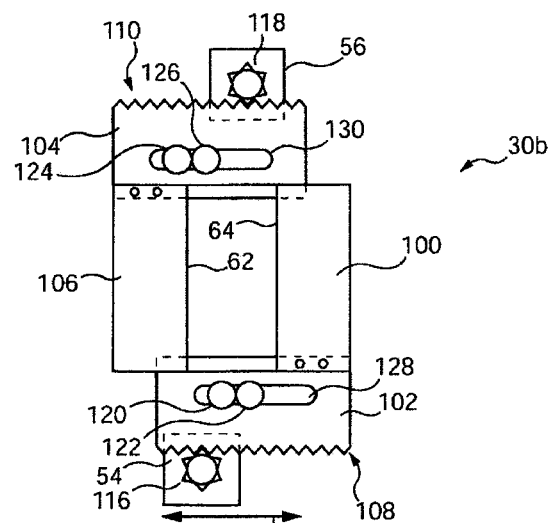

FIGS. 2a and 2b show the means of collimation (30) which enables the collimation slot to be geometrically variable.

The means for adjustment is set up so that it is able to change, on command, the geometry of the slot and, in particular, its length along two directions which are perpendicular to each other, for example, horizontal and vertical.

More specifically, the adjustment means adapted to change the length of the slot along one direction is independent of those adapted to change the length in the other direction, offering thusly greater flexibility in the adjustment.

In the example illustrated, the x-ray equipment comprises four independent means of adjustment (50, 52, 54, 56) to independently change the position of each of the four edges (58, 60, 62, 64) defining the collimation slot.

On the support positioned in front of the output window of FIG. 1, are successively superimposed the arrangement (30a) of FIG. 2a, then that (30b) of FIG. 2b.

These arrangements are not shown in a superimposed fashion for reasons of clarity.

More specifically, the arrangement (30a) of FIG. 2a comprises two edges (58, 60) of two plates (66. 68) placed opposite of each other (for example rectangular in shape) and which are each attached respectively to another plate (70, 72) positioned perpendicularly.

Each pair of plates (66, 70 and 68, 72) form in this way an L or an L turned 180°.

The second plate (70, 72) of each pair is supplied, on one of its edges which is opposite to the one against which the first plate is fixed, with a longitudinal row of teeth (74, 76).

A means of moving the edge (58) (respectively 60) comprising a motor (50) (respectively 52) equipped with a toothed sprocket (78) on the output shaft (respectively 80).

This sprocket works with the teeth (76) (respectively 74) to cause the movement of plates (72 and 68) in the direction D1 in either direction depending on the direction of rotation of the sprocket.

A light guide (82) (respectively 84) is provided for on the second plate (72) (respectively 70) and two guide pins (86, 88) (respectively 90, 92) interdependent with the aforementioned support are positioned in this groove to guide the movement longitudinally of the corresponding plate and therefore the corresponding edge.

This arrangement allows, by adjusting the space between the opposing edges (58 and 60) in direction D1, adjusting one of the dimensions of the slot and thus its length in one direction.

In the identical manner, the arrangement shown in 30b in FIG. 2b allows, by adjusting the space between the opposing edges (62 and 64) in direction D2, adjusting one of the dimensions of the slot in the other direction.

Figure 2C:
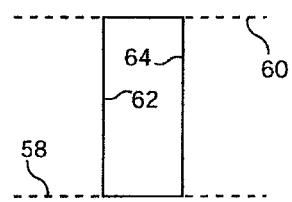
FIG. 2c diagrammatically illustrates a collimation slot obtained with the means of FIGS. 2a and 2b.

Thus, by bringing the edges (62 and 64) closer and by moving the edges (58 and 60) apart of the slot in a lengthwise fashion along direction D1. A slot that follows along axis Z shown in FIG. 2c is obtained in this manner.

To the contrary, if the edges (62 and 64) are moved apart and edges (58 and 60) are brought together, the lengthwise shape of the slot is carried out along direction D2. One thus obtains an elongated slot following an axis perpendicular to axis Z.

We can also adjust the spacing of opposite edges (58, 60) and (62, 64) in order to obtain a slot in the form of a square or close to such a form.

The different elements shown in FIG. 2b, i.e., the first and second plates (100, 102) (respectively 104, 106), the grooves (108) (respectively 110), the motor (54) (respectively 56) and its toothed sprocket (116) (respectively 118), as well as the guide pins (120, 122) (respectively 124, 126) in the guide light (128) (respectively 130) are identical to their corresponding parts in FIG. 2a but that are only shifted 90°.

Figure 3A:
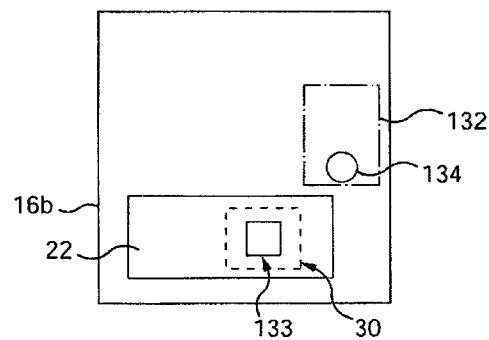
FIG. 3a diagrammatically illustrates a view of the surface of the end of the device of FIG. 1.

The equipment of FIG. 1 also comprises, as shown in FIG. 3a (front view of the arm 16b), the means of acquisition (132) of at least one photographic image of the object placed between the x-ray generator and the sensor, i.e., the patient's head.

In FIG. 3a, on the lower part of the arm (16b), the support (22) placed in front of the generator (18), is also shown, as well as the means collimation (30) shown with a dotted line and a collimation slot (133) placed before the x-ray output slot.

The acquisition means (132) which take, for example, the form of a digital image capture device (such as a photographic camera fitted with a lens (134)) are positioned as close as possible to the x-ray emission chamber. In the example of FIG. 3a, the means (132) are placed above the generator and are shifted laterally with respect to the latter. Nevertheless, other layouts are possible, based on the constraints of the environment.

Figure 3B:
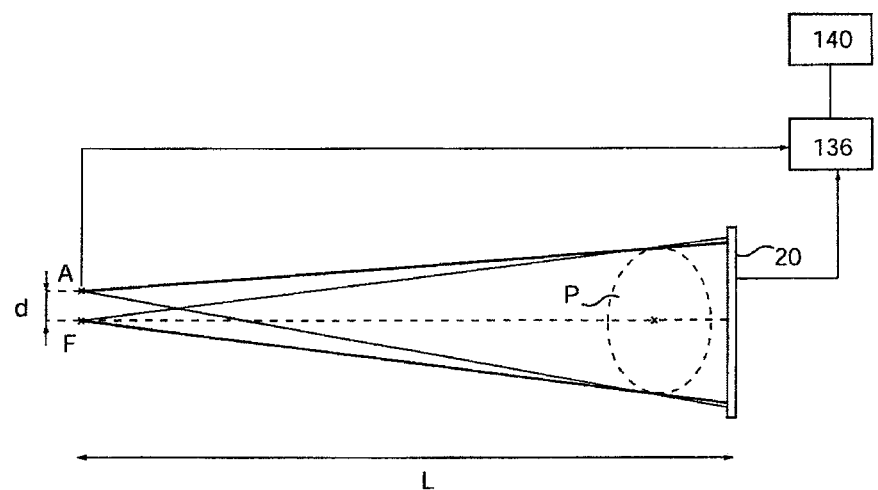
FIG. 3b shows in a diagrammatical fashion the layout of the means of acquisition of a photographic image, of the x-ray emission chamber, of the head of a patient and of the sensor.

These means (132) are also represented in FIG. 3b by letter A, while the emission chamber is represented by the letter F.

The distance between these means of photographic image acquisition and the generator chamber is small in comparison with the distance L between the chamber and the sensor (20).

As an example, distance d is equal to 5 cm and distance L is equal to 170 mm.

Thus, by positioning the means of image acquisition as close as possible to the generator chamber, in light of the available space around the means of collimation placed in front of the of x-ray emission slot, we ensure that the angle under which the photographic image(s) of the head of the patient are taken is very close to the angle at which the cone x-ray beam is emitted viewed from the sensor.

As an example, a shift of less than 5 degrees will give good results.

Correspondingly, the photographic image of the patient's head, and the cephalometric image are superimposable.

As diagrammatically illustrated in FIG. 3b, the photographic and cephalometric images are provided respectively by the means of acquisition (A) and by the sensor (20) to a data processing unit (136) including a means for storing the images.

A screen (140) to display the images acquired individually and superimposed is also connected to the processing unit.

The processing unit (136) and the display means (140) make part of the x-ray equipment illustrated in FIG. 1.

The processing unit (136) ensures control of the operation of the equipment (10).

This unit may be, for example, a PC computer.

It should be noted that the dimensions of the pixel matrix of the sensor (20) encompass the dimensions of the x-ray beam projection that irradiated the head (P) of the patient.

Figure 4:
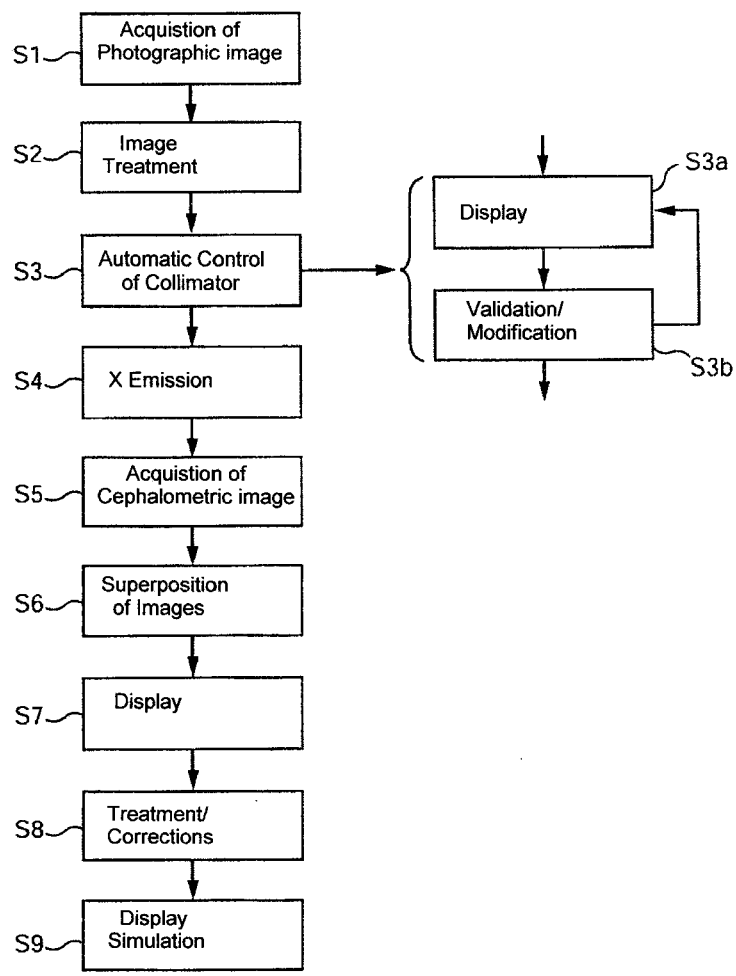
FIG. 4 illustrates an algorithm of the method to produce a cephalometric image.

FIG. 4 represents an algorithm outlining the main stages of a method according of the invention and that may be implemented for example, by the equipment (10).

This algorithm is for example, is stored in a memory area of the processing unit (136) and is run on command.

To implement the method according of the invention, the patient should be placed between the x-ray generator and the sensor illustrated in FIG. 1 and that his/her head should be immobilized close to the sensor, in other words, at a good distance from the generator, for example, around 150 cm.

When the practitioner starts the equipment, for example from a keyboard and a pointing interface such as a mouse, which are not shown in the figures but that interact with the processing unit (136) and the screen (140) of FIG. 3b, a mode of acquisition of one or more photographic images of the patient's head (face view or profile view) is started during a first stage (S1).

The image(s) are stored.

Through the second stage (S2), processing of an image is provided for in order to preserve only the outline of the patient's head.

In fact, these outlines are sufficient to supply the necessary information to the equipment user.

This processing is performed by the processing unit (136) which determines the dimensions of the outline of the head, among other things.

The algorithm comprises a third stage (S3) controlling the means of collimation with respect to the photographic image(s) acquired in stage S1 and, in particular, the dimensions of the patient's head obtained in stage S2.

This ensures that the dimensions of the X-ray beam emitted by the chamber (F) and collimated by the means of collimation are adjusted to the dimensions of the outline of the patient's head.

Thus, the cephalometric image(s) that one wishes to carry out using the equipment will be perfectly adapted to the dimensions of the patient's head.

Correspondingly, the patient's head will not be truncated on the image(s) and the patient will not receive useless doses of radiation as was the case in the past.

From the practical point of view, control of the means of collimation consists of setting the dimensions of the x-ray beam so that it is adapted to the dimensions of the outline of the patient's head.

This setting includes, more in particular, the adjustment of the length of the collimation slot of the means 30a and 30b illustrated in FIGS. 2a and 2b, in a perpendicular direction between them. This setting is controlled by the processing unit (136) of FIG. 3b from the dimensions of the outline of the head calculated in stage S2.

Optionally, the algorithm may include a stage S3a of display on the screen (140) of the edges of the collimation slot projected once it is set to the dimensions of the outline of the patient's head, and that are superimposed upon the outline of the head.

This stage of display makes it possible to ensure that the automatic control of the collimator at the patient's head is correct and may be validated during stage S3b.

Under the hypothesis where the edges of the collimation slot shift, it will not be adapted to the dimensions of the outline of the patient's head, or perhaps that this shift will be too great or too small with respect to the head, stage S3b also provides for the modification of the setting of the collimation slot in order to obtain an adjustment with respect to the outline of the patient's head. Alternatively, stage S3b makes it possible to return to the collimation slots pre-programmed by default.

Stage S3b is then followed by the display stage S3a so that the user of the device may see the new setting which has been carried out.

Then, stage S3b is performed again so the user can validate the setting.

The algorithm then comprises an S4 stage of the emission of the cone x-ray beam, this beam being collimated by the collimation slot the setting of which was obtained and validated in stage S3.

Thus, the collimated beam is perfectly adapted to the dimensions of the outline of the patient's head.

Figure 5A:
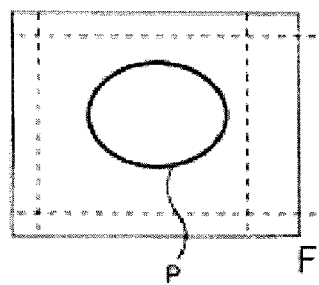
FIGS. 5a and 5b shows in a diagrammatical fashion the radiological project of a beam irradiating a patient's head with the un-adjusted edges of a collimator.

FIG. 5a shows the display on the screen of the patient's head (P) and of the cone projection of the edges of the slot when the automatic control according to the invention has not been performed.

Figure 5B:
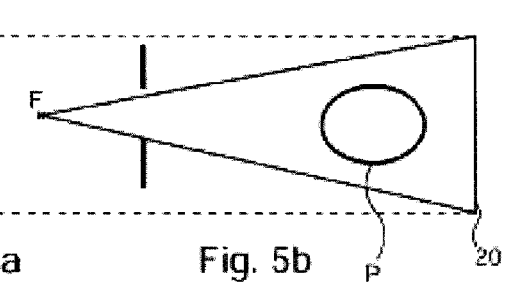

FIG. 5b shows the position corresponding to the edges of the slot, of the head, and of the sensor in the layout shown in FIG. 3b.

In this position, the patient receives an overdose of radiation.

Figure 5C:
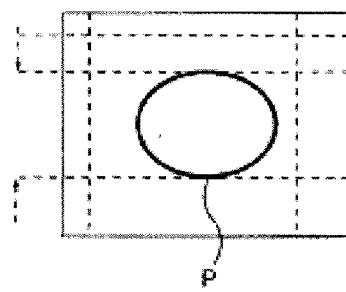
FIGS. 5c and 5d show in a diagrammatical fashion the radiological project of a beam irradiating a patient's head with the adjusted edges of the collimator.

FIG. 5c shows the display on the screen of the head (P) of the cone projection of the edges of the slot after the automatic control with respect to the photographic image has been previously performed.

Figure 5D:
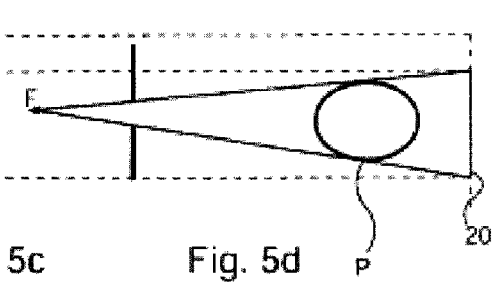

The means of collimation is represented in FIG. 5d in an adjusted position obtained through the automatic control.

The configuration of the x-ray beam is thus adapted to the patient's head and the latter receives an optimal dose of radiation. The x-ray projection of the beam which irradiated the head is recorded on the active surface of the sensor (20).

Stage S5 provides for the acquisition of one or more cephalometric images of the patient's head. This or these images are acquired instantaneously so that the patient has no opportunity to move, thus avoiding distortions. It should be noted that a shot will be taken, for example, in ½ s.

In the embodiment described, the photographic and cephalometric images correspond to views of the profile of the patient's head.

Figure 6:
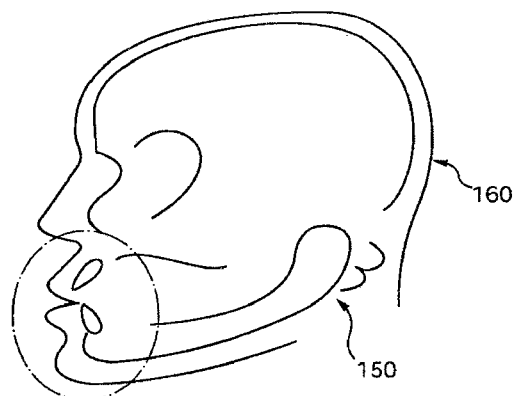
FIG. 6 illustrates in a diagrammatical fashion the superposition of the cephalometric and photographic images.

In stage S6, after acquiring a cephalometric image (150), the superimposition of the cephalometric image (150) and the photographic image (160) is provided for as shown in FIG. 6.

The photographic image (160) makes the soft tissue of the patient's head (nose, lips, chin . . . ) appear, while the cephalometric image (150) reveals the hard tissue (bone, teeth . . . ).

It should be noted that the superimposition of images is carried out in a particularly reliable and accurate manner due to positioning the means of acquisition of the photographic image at a very short distance from the X-ray emission chamber.

It should be noted that superimposing the photographic image onto the cephalometric image needs to apply a geometric conversion based on recognition of the profile and target point in order to get a perfect match. For example, we can use the device's (21) patient support arms in FIG. 1 for this purpose.

As already mentioned, views from the sensor (20) illustrated in FIG. 3b, the two photographic and cephalometric images may be considered to have been taken at the same camera angle.

An almost perfect line up between the two images makes it possible to correctly position within the same view (FIG. 6) both the soft tissue and the hard tissue in relation to each other.

This superimposition of images is followed by step S7 of viewing the images thus superimposed which is shown in the aforementioned FIG. 6.

This display takes place, for example, on the screen (140) of FIG. 3b.

The image thus obtained on the display screen allows the practitioner, for example, an orthodontist, to establish a diagnosis by identifying certain defects needing to be corrected, for example, in the patient's jaw.

He may thus determine the corrections that will be provided to the jaw as well as the appropriate treatment.

Figures 7, 8:
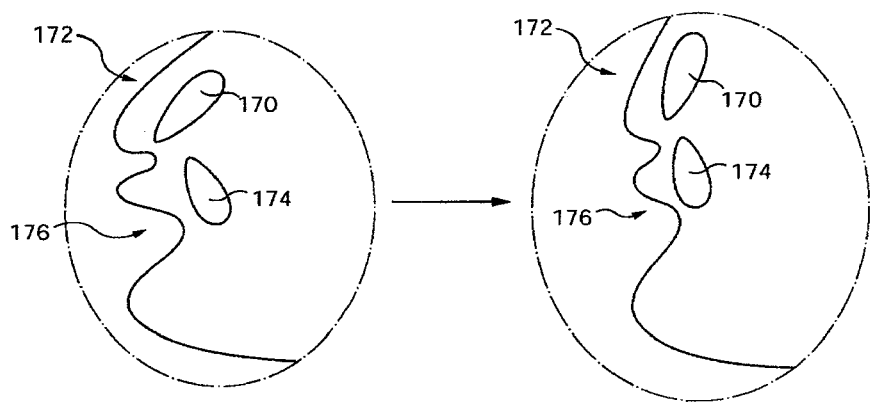
FIG. 7 illustrates in a diagrammatical fashion an enlarged view of a part of the image of FIG. 6.
FIG. 8 illustrates in a diagrammatical fashion the hard tissue of the cephalometric image reshaped by calculation.

In the example shown in FIG. 6, and shown as a magnified view in FIG. 7, the implantation of the incisor (170) in the jaw of the patient is such that the latter is particularly inclined from the vertical toward the front of the patient's mouth, which causes a deformation of the upper lip (172).

In the same way, the tooth (174) is implanted in the lower jaw in such a way that it is strongly tilted towards the vertical direction in the front of the mouth, which also causes a deformation of the lower lip (176).

On the basis of this report, the practitioner will take measures and possibly scans in order to determine the corrections to be made to the jaw of the patient, as well as the appropriate treatment (for example, installation of an appliance in order to correct the position of the teeth (170 and 174)).

This stage corresponds to stage S8 of the algorithm.

The following stage S9 makes it possible to display, as a preview, the effects through time of the treatment recommended by the practitioner for the patient's jaw.

The reshaping of the hard tissue in the cephalometric image is obtained by calculation, from the data selected by the practitioner when he determines the corrections to be made and the appropriate treatment, This stage is performed by the processing unit (136) and corresponds to running an algorithm of a known type and available on the market. For example software marketed by the company Practice Works would work.

The effects thus simulated on the hard tissue of the cephalometric image are illustrated in FIG. 8.

Similarly, the manner in which the soft tissues (the lips in particular) are distorted correspondingly over time is obtained through a morphing algorithm, of a known type, which is also implemented by the processing unit (136).

The display of the effects thus simulated on the soft tissues of the patient is also illustrated in FIG. 8 corresponding to the superimposition of the two images, after reshaping each of them.

It should be noted that the reshaping of the hard tissue in the cephalometric image and the reshaping of the soft tissues of the photographic image are performed independently from each other insofar as, in the image of FIG. 6, the superimposition of the two images is shown, each of them correspond to a set of separate data and thus it is possible to process them separately.

Due to the display of this simulation, the practitioner, as well as the patient, are both able to appreciate the impact of the treatment recommended by the practitioner, in a particularly realistic manner.

What is claimed:
1. A dental cephalometric x-ray unit comprising:
   an X-ray generator adapted to generate an X-ray beam in the direction of a patient's head;
   a means of collimation adapted to provide given dimensions to the generated X-ray beam to generate a collimated X-ray beam;

a sensor, disposed facing the generator, receiving the x-ray projection of the collimated beam irradiating the patient's head to generate a cephalometric image of the patient's head;

means to acquire at least one photographic image of the patient's head; and means of automatic control of the means of collimation according to the at least one photographic image so that the given dimensions of the collimated X-ray beam are adjusted to dimensions of the patient's head determined from the at least one photographic image.

2. The dental x-ray unit according to claim 1, wherein the sensor is a pixel matrix surface sensor with dimensions that encompass the dimensions of the X-ray beam projection that irradiates the patient's head.

3. The dental x-ray unit according to claim 1, wherein the X-ray generator includes an X-ray emission chamber, and the means to acquire at least one photographic image is positioned adjacent the chamber.

4. The dental x-ray unit according to claim 1, wherein the means of collimation includes collimator having an adjustable slot.

5. The dental x-ray unit according to claim 4, wherein the adjustable slot collimator comprises means to adjust the length of the slot perpendicularly between them.

6. The dental x-ray unit according to claim 5, wherein the means to adjust is independent directionally.

7. The dental x-ray unit according to claim 4, wherein the slot is delimited by four edges that slide in a manner that is independent from each other.

8. The dental x-ray unit according to claim 1, further comprising means to obtain an outline of the patient's head from the at least one photographic image.

9. The dental x-ray unit according to claim 8, wherein the means of automatic control is adapted to automatically control the means of collimation in function of the dimensions of the outline of the patient's head wherein the dimensions of the collimated X-ray beam are adjusted to the dimensions of the outline.

10. A method to produce a cephalometric image of the head of a patient, comprising:

generating, by an X-ray generator, an X-ray beam in the direction of a patient's head;

collimating the generated X-ray beam to confer to it given dimensions;

directing the collimated beam that irradiates the patient's head toward a sensor facing the radiological projection;

generating a cephalometric image from the received radiological projection;

acquiring at least one photographic image of the patient's head; and automatically controlling the collimation of the X-ray beam according to the at least one photographic image so that the given dimensions of the collimated X-ray beam are adjusted to dimensions of the patient's head determined from the at least one photographic image.

11. The method according to claim 10, wherein the sensor is a pixel matrix surface sensor with dimensions that encompass the dimensions of the x-ray beam projection that irradiates the patient's head; and the acquisition of the radiological projection is performed instantly.

12. The method according to claim 10, wherein the X-ray generator comprises an x-ray emission chamber; and the acquisition of at least one photographic image is performed from a first distance from the x-ray emission chamber so a ratio of the first distance to a second distance from the x-ray emission chamber to the patient's head is at least 1 to 15.

13. The method according to claim 10, wherein the automatic controlling the collimation of the X-ray beam according to the at least one photographic image includes the adjustment of the dimensions of the beam.

14. The method according to claim 13, wherein the adjustment of the dimensions of the beam comprises means to adjust the length of a collimation slot perpendicularly between them.

15. The method according to claim 10, further comprising obtaining an outline of the patient's head from the at least one photographic image.

16. The method according to claim 15, wherein the automatic control of the collimation is performed as a function of the dimensions of the outline of the patient's head so that the dimensions of the collimated X-ray beam are adjusted to the dimensions of the outline.

* * * * *